US00PP16750P2

(12) United States Plant Patent
Michalik

(10) Patent No.: US PP16,750 P2
(45) Date of Patent: Jul. 4, 2006

(54) ***GERANIUM* PLANT NAMED 'PACASAL'**

(50) Latin Name: *Pelargonium×domesticum*
Varietal Denomination: Pacasal

(75) Inventor: Andrea Michalik, Dresden (DE)

(73) Assignee: Elsner Pac Jungpflazen, Dresden (DE)

( * ) Notice: Subject to any disclaimer, the term of this patent is extended or adjusted under 35 U.S.C. 154(b) by 52 days.

(21) Appl. No.: 11/077,416

(22) Filed: Mar. 10, 2005

(51) Int. Cl.
*A01H 5/00* (2006.01)

(52) U.S. Cl. ..... Plt./331
(58) Field of Classification Search ..... Plt./331
See application file for complete search history.

*Primary Examiner*—Kent Bell
(74) *Attorney, Agent, or Firm*—C. A. Whealy

(57) ABSTRACT

A new and distinct cultivar of Regal *Geranium* plant named 'Pacasal', characterized by its upright plant habit; vigorous growth habit; freely basal branching habit; and large dark pink-colored flowers.

1 Drawing Sheet

Botanical designation: *Pelargonium×domesticum.*
Cultivar Denomination: 'Pacasal'.

CROSS-REFERENCE TO RELATED APPLICATIONS

The present application is co-pending with the following application: *Geranium* Plant Named 'Pacared'; Andrea Michalik, applicant.

BACKGROUND OF THE INVENTION

The present invention relates to a new and distinct cultivar of Regal *Geranium* plant, botanically known as *Pelargonium×domesticum,* and hereinafter referred to by the name 'Pacasal'.

The new Regal *Geranium* is a product of a planned breeding program conducted by the Inventor in Dresden, Germany. The objective of the breeding program was to develop new Regal *Geraniums* that did not require a cooling treatment for flower development.

The new Regal *Geranium* originated from a cross-pollination made by the Inventor during 2001 of two proprietary selections of *Pelargonium×domesticum,* not patented. The cultivar Pacasal was discovered and selected by the Inventor as a flowering plant within the progeny from the stated cross-pollination in a controlled environment in Dresden, Germany in 2002.

Asexual reproduction of the new cultivar by terminal cuttings in a controlled environment in Dresden, Germany since 2002 has shown that the unique features of this new Regal *Geranium* are stable and reproduced true to type in successive generations of asexual reproduction.

SUMMARY OF THE INVENTION

The following traits have been repeatedly observed and are determined to be the unique characteristics of 'Pacasal'. These characteristics in combination distinguish 'Pacasal' as a new cultivar and distinguish it from other known Regal *Geranium* cultivars:

1. Upright plant habit.
2. Vigorous growth habit.
3. Freely basal branching habit.

4. Large dark pink-colored flowers.
5. Does not require cooling treatment for flower development.

Plants of the new Regal *Geranium* differ primarily from plants of the parent selections in flower coloration.

Plants of the new Regal *Geranium* can be compared to plants of the cultivar Pacared, disclosed in U.S. Plant patent application Ser. No. 11/077,417. In side-by-side comparisons conducted in Dresden, Germany, plants of the new Regal *Geranium* differed from plants of the cultivar Pacared in the following characteristics:

1. Plants of the new Regal *Geranium* had more flower umbels per plant than plants of the cultivar Pacared.
2. Plants of the new Regal *Geranium* and the cultivar Pacared differed in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Regal *Geranium*. The photograph comprises a side perspective view of a typical flowering plant of 'Pacasal' grown in a container.

DETAILED BOTANICAL DESCRIPTION

Plants of the cultivar Pacasal have not been observed under all possible environmental conditions. The phenotype may vary somewhat with variations in environment, such as temperature and light intensity, without, however, any variance in genotype.

The aforementioned photograph, following observations and averaged measurements describe plants grown during the spring in containers in Dresden, Germany, and under commercial practice in a glass-covered greenhouse with day temperatures about 18° C., night temperatures about 16° C. and light levels less than 60,000 lux. Plants used for the photograph and the description were about five months old. In the following description, color references are made to The Royal Horticultural Society Colour Chart, 1995 Edition, except where general terms of ordinary dictionary significance are used.

Botanical classification: *Pelargonium×domesticum* cultivar Pacasal.

Parentage:

*Female, or seed, parent.*—Proprietary selection of *Pelargonium×domesticum,* not patented.

*Male, or pollen, parent.*—Proprietary selection of *Pelargonium×domesticum,* not patented.

Propagation:

*Type cutting.*—Terminal cuttings.

*Time to initiate roots.*—Summer: About 12 days at 23° C. Winter: About 14 days at 23° C.

*Time to produce a rooted young plant.*—Summer: About 30 days at 23° C. Winter: About 32 days at 23° C.

*Root description.*—Fibrous, medium in thickness; white in color.

*Rooting habit.*—Freely branching, moderately dense.

Plant description:

*General appearance.*—Upright plant habit; uniformly mounded; inverted triangle; densely foliated.

*Growth and branching habit.*—Vigorous growth habit. Freely basal branching habit with about seven to nine lateral branches per plant.

*Plant height, to top of umbels.*—About 27 cm.

*Plant height, to top of foliar plane.*—About 20 cm.

*Plant width.*—About 25 cm.

*Lateral branches.*—Length: About 2 to 15 cm. Diameter: About 0.8 to 1.2 cm. Internode length: About 0.5 to 1.5 cm. Texture: Pubescent. Color: Close to 144A.

*Foliage description.*—Arrangement: Alternate or opposite; simple. Length: About 8 cm. Width: About 11 cm. Shape: Palmately lobed. Apex: Acute. Base: Cordate; open. Margin: Biserrate; undulate. Venation pattern: Palmate. Texture, upper and lower surfaces: Pubescent; leathery. Color: Developing foliage, upper and lower surfaces: 144A. Fully expanded foliage, upper surface: 137C; venation, similar to lamina. Fully expanded foliage, lower surface: 137C; venation, 147C. Petiole: Length: About 5 to 9 cm. Diameter: About 2 to 4 mm. Texture, upper and lower surfaces: Pubescent. Color, upper and lower surfaces: Close to 144A.

Flower description:

*Flower arrangement.*—Single rotate flowers arranged in rounded hemispherical umbels arising from apical leaf axils. Umbels displayed above the foliage on strong peduncles. Flowers face upright to outward. Flowers not persistent. Flowers not fragrant.

*Quantity of flowers.*—About 7 to 15 umbels per plant each umbel with about seven flower buds and open flowers.

*Flowering season.*—Year-round under greenhouse conditions. In the garden in Dresden, Germany, flowering is continuous during the spring and summer. Plants do not require a cooling treatment for flower development.

*Flower longevity.*—Individual flowers last about six to eight days on the plant.

*Umbel height.*—About 5.5 cm.

*Umbel diameter.*—About 8 cm.

*Flower diameter.*—About 5 cm.

*Flower depth* (*height*).—About 2.5 cm.

*Flower buds.*—Length: About 2 cm. Diameter: About 8 mm. Shape: Elliptic. Color: Close to 144A.

*Petals.*—Quantity per flower: About five. Length: About 4 cm. Width: About 3 cm. Shape: Obovate. Apex: Rounded. Base: Attenuate. Margin: Entire. Texture, upper and lower surfaces: Smooth, glabrous; satiny. Color: When opening, upper surface: Close to 52A; towards the base, close to 59A; at the base, close to 155D; venation, 59A. When opening, lower surface: Close to 52C; at the base, close to 155D; venation, 59A. Fully opened, upper surface: Close to 52B; towards the base, close to 59A; at the base, close to 155D; venation, 59A. Fully opened, lower surface: Close to 52C; at the base, close to 155D; venation, 59A.

*Sepals.*—Quantity per flower: Five, arranged in a single whorl. Length: About 1.1 cm. Width: About 5 mm. Shape: Lanceolate. Apex: Acute. Base: Attenuate. Margin: Entire; undulate. Texture, upper and lower surfaces: Pubescent. Color, upper and lower surfaces: Close to 144A.

*Peduncle* (*umbel stem*).—Length: About 4.5 cm. Diameter: About 3 mm. Strength: Strong. Texture: Pubescent. Color: Close to 144A.

*Pedicel* (*individual flower stem*).—Length: About 1.5 to 2 cm. Diameter: About 2 mm. Strength: Strong. Texture: Pubescent. Color: Close to 144A.

*Reproductive organs.*—Androecium: Stamen quantity per flower: About seven. Anther shape: Elliptic. Anther color: Dark red. Pollen amount: Abundant. Pollen color: Orange. Gynoecium: Pistil quantity per flower: One. Pistil length: About 2 cm. Stigma shape: Parted. Stigma color: Red. Style length: About 1.1 cm. Style color: Dark red. Ovary color: Close to 144A.

*Seed.*—Length: About 2 to 3 mm. Diameter: About 1 mm. Shape: Elliptic. Color: Brown.

Disease/pest resistance: Plants of the new Regal *Geranium* have not been observed to be resistant to pathogens and pests common to Regal *Geraniums.*

Garden performance: Plants of the new Regal *Geranium* have been observed to tolerate rain, wind, and temperatures ranging from 10 to 25° C.

It is claimed:

1. A new and distinct cultivar of Regal *Geranium* plant named 'Pacasal', as herein illustrated and described.

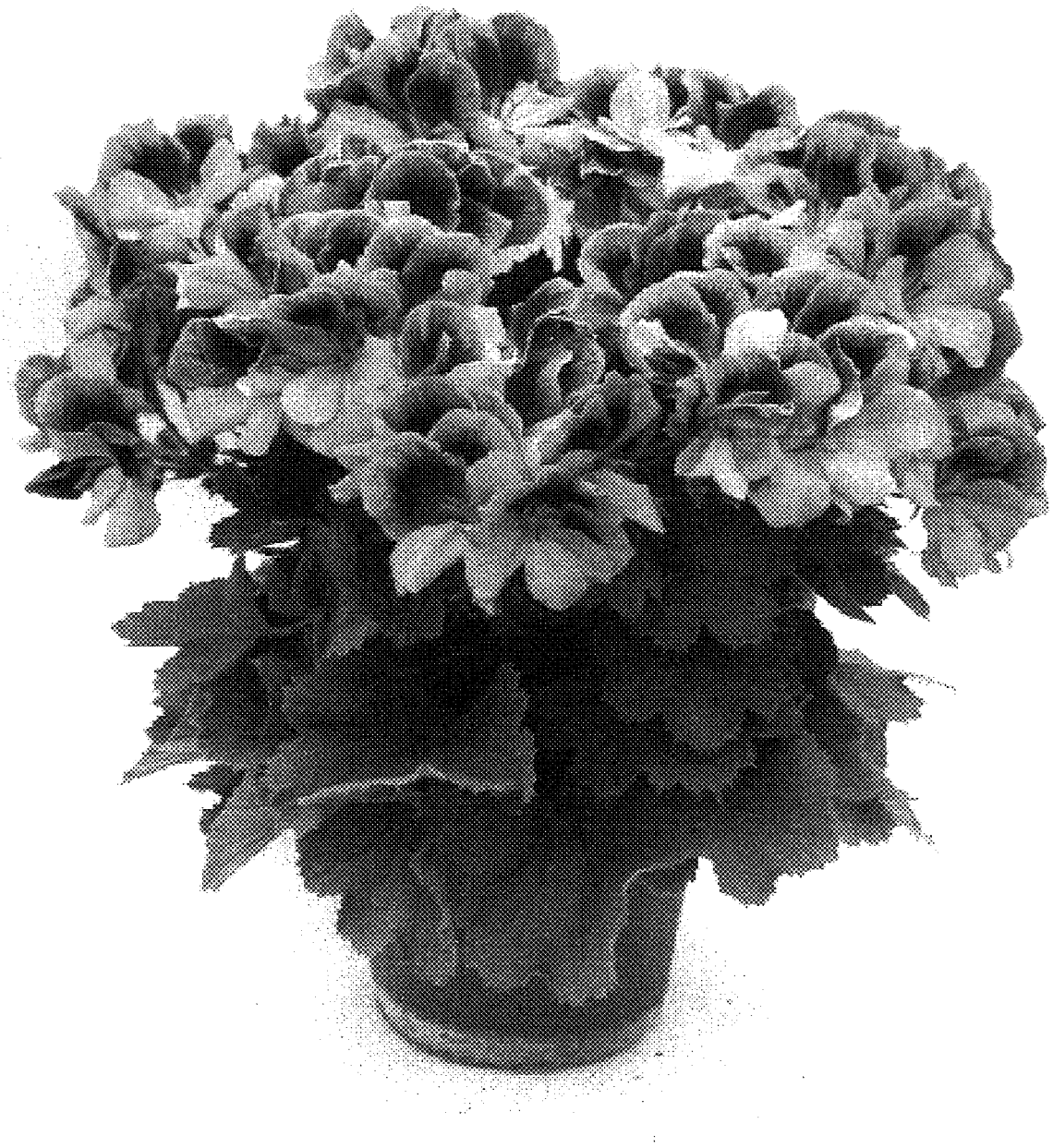

* * * * *